(12) United States Patent
Ramalingam

(10) Patent No.: US 6,476,234 B2
(45) Date of Patent: Nov. 5, 2002

(54) METHODS OF SYNTHESIZING HETEROATOM-BEARING LIGANDS AND INTERMEDIATE USED THEREFOR

(75) Inventor: Kondareddiar Ramalingam, Dayton, NJ (US)

(73) Assignee: Bracco International B.V. (NL)

( * ) Notice: Subject to any disclaimer, the term of this patent is extended or adjusted under 35 U.S.C. 154(b) by 0 days.

(21) Appl. No.: 10/086,290

(22) Filed: Mar. 1, 2002

(65) Prior Publication Data

US 2002/0143190 A1 Oct. 3, 2002

Related U.S. Application Data

(62) Division of application No. 09/818,301, filed on Mar. 27, 2001, now Pat. No. 6,384,232.

(51) Int. Cl.⁷ .............................................. C07D 403/14
(52) U.S. Cl. .................................................... 548/312.1
(58) Field of Search ...................................... 548/312.1

(56) References Cited

U.S. PATENT DOCUMENTS

| | | | |
|---|---|---|---|
| 5,608,110 A | 3/1997 | Ramalingam et al. | ...... 564/253 |
| 5,627,286 A | 5/1997 | Ramalingam et al. | ... 548/341.1 |
| 5,656,254 A | 8/1997 | Ramalingam et al. | ..... 424/1.65 |
| 5,665,329 A | 9/1997 | Ramalingam et al. | ..... 424/1.65 |
| 5,741,912 A | 4/1998 | Ramalingam et al. | ... 548/341.1 |

*Primary Examiner*—Joseph K. McKane
*Assistant Examiner*—Kamal Saeed
(74) *Attorney, Agent, or Firm*—Clark & Elbing LLP

(57) ABSTRACT

The invention provides improved and simplified methods of synthesizing ligands containing a heteroatom-bearing bridge using a novel intermediate compound. The ligands may be used to form metal complexes that are useful in diagnostic and therapeutic applications.

6 Claims, No Drawings

METHODS OF SYNTHESIZING HETEROATOM-BEARING LIGANDS AND INTERMEDIATE USED THEREFOR

CROSS REFERENCE TO RELATED APPLICATIONS

This application is a divisional of and claims priority from U.S. patent application Ser. No. 09/818,301, filed Mar. 27, 2001 now U.S. Pat. No. 6,384,232.

FIELD OF THE INVENTION

The present invention relates to compounds containing a heteroatom-bearing bridge, and to complexes of these compounds with metals. In particular, the invention relates to improved and simplified methods of synthesizing such compounds using a novel intermediate.

BACKGROUND OF THE INVENTION

Metal complexes, such as those containing radioactive metals, are useful as diagnostic and therapeutic agents. Complexes containing bioactive moieties capable of being selectively taken up at a desired site to facilitate evaluation or treatment of a subject are of particular interest. For example, U.S. Pat. No. 5,608,110 discloses compounds containing a heteroatom-bearing bridge which may be complexed with a metal and used in diagnostic and therapeutic methods. Although U.S. Pat. No. 5,741,912 discloses methods for preparing a variety of such compounds, there remains a need for simplified methods of synthesizing these compounds. The present invention addresses the need in the art for improved and simplified methods of synthesizing ligands for use in metal complexes, particularly complexes containing hypoxia-localizing moieties.

SUMMARY OF THE INVENTION

The present invention features methods of making compounds, also referred to herein as ligands, using a novel intermediate. In particular, the invention features improved and simplified methods of making compounds having the structure of Formula I:

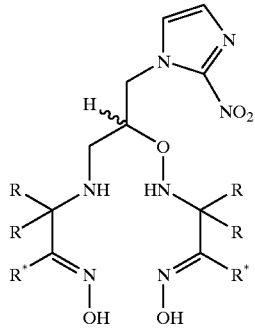

I where all R and R* groups are independently:
(i) $R^2$;
(ii) halogen, especially fluoro;
(iii) —$OR^2$;
(iv) —C(O)—$OR^2$;
(v) —C(O)—$N(R^2)_2$;
(vi) —$N(R^2)_2$;
(vii) -alkyl-C(O)—$OR^2$;
(viii) -alkyl-C(O)—$N(R^2)_2$;
(ix) -alkyl-$N(R^2)_2$;
(x) -aryl-C(O)—$OR^2$;
(xi) -aryl-C(O)—$N(R^2)_2$;
(xii) -aryl-$N(R^2)_2$;
(xiii) acyl;
(xiv) acyloxy;
(xv) heterocyclo;
(xvi) hydroxyalkyl;
(xvii) —$SO_2$—$R^2$;
(xviii) -alkyl-$SO_2$—$R^2$;
(xix) —$(A)_p$—$R^3$, where A is a linking group, p is 0 or a positive integer, and $R^3$ is a bioactive moiety; or
(xx) two R groups, or an R group and an R* group, taken together with the one or more atoms to which they are bonded, form a saturated or unsaturated, spiro or fused, carbocyclic (such as fused 1,2-phenyl) or heterocyclic ring which may be unsubstituted or substituted by one or more groups selected from the groups (i) to (xix) above;

with the proviso that a carbon atom bearing an R group is not directly bonded to more than one heteroatom; and $R^2$ is independently hydrogen, alkyl, alkenyl, alkynyl, or aryl.

The synthetic method of the invention provides compounds of Formula I through the following novel intermediate compound (Formula II):

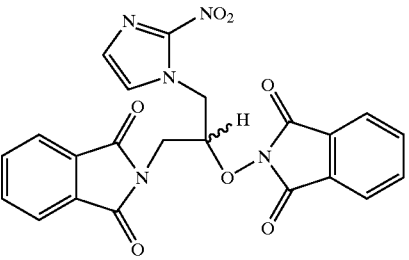

Formula II

In the synthetic scheme of the present invention, the intermediate compound of Formula II may be isolated and purified. The synthetic method of the invention also provides stereoisomers of the intermediate compound, such as 2-{(1R)-2-(1,3-dioxoisoindolin-2-yl)-1-[(2-nitroimidazolyl)methyl]ethoxy}isoindoline-1,3-dione:

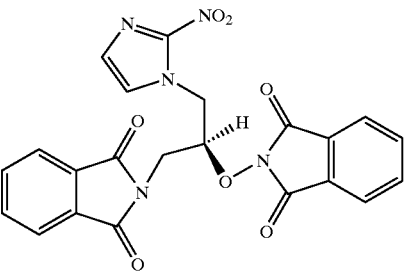

and 2-{(1S)-2-(1,3-dioxoisoindolin-2-yl)-1-[(2-nitroimidazolyl)methyl]ethoxy}isoindoline-1,3-dione:

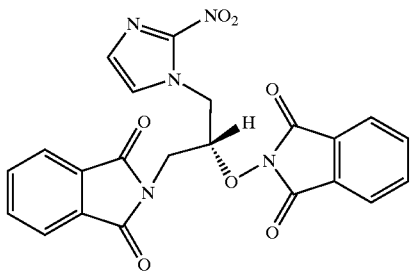

The intermediate compound of Formula II may also be used to make a variety of compounds of Formula I. Preferred compounds are obtained by first reacting the intermediate of Formula II with hydrazine of the formula:

to yield -1-[3-amino-2-(aminooxy)propyl]-2-nitro-1H-imidazole dihydrochloride, which is then reacted with a compound of Formula III. Compounds of Formula III may include compounds of Formula IIIa or Formula IIIb, set forth below, or a mixture of these two compounds:

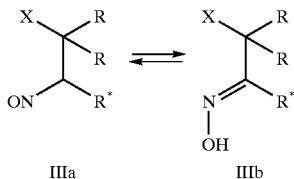

where X is halogen (preferably Cl, Br or I) and R and R* are defined above, to yield a compound of Formula I. A preferred compound of Formula III is 3-chloro-3-methyl-2-nitrosobutane.

A preferred compound of Formula I is compound Ia, 3,3,9,9-tetramethyl-6-[(2-nitro-1H-imidazol-1-yl)methyl]-5-oxa-4,8-diazaundecane-2,10-dione dioxime:

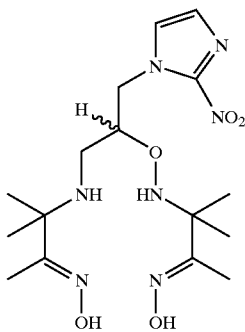

The invention also provides methods of synthesizing stereoisomers of compound Ia, such as (S)-(−)-3,3,9,9-tetramethyl-6-[(2-nitro-1H-imidazol-1-yl)methyl]-5-oxa-4,8-diazaundecane-2,10-dione dioxime:

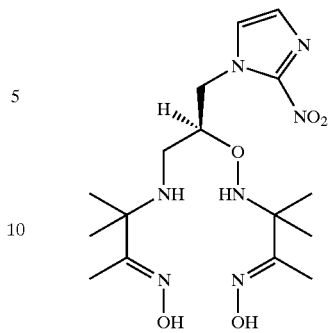

and R-(−)-3,3,9,9-tetramethyl-6-[(2-nitro-1H-imidazol-1-yl)methyl]-5-oxa-4,8-diazaundecane-2,10-dione dioxime:

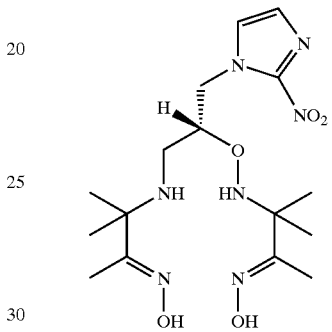

Compounds of Formula I may be complexed with metals, preferably radioactive metals discussed below, such as rhenium or technetium, and used in diagnostic and therapeutic methods. Compounds of Formula I are derivatized with a 2-nitro-imidazole hypoxia-localizing moiety. This hypoxia-localizing moiety retains the biochemical behavior and affinity of the free moiety. Compounds of Formula I are capable of rapidly providing increased amounts of a desired radionuclide selectively to targeted areas, may be labeled at ambient temperature with suitable radionuclides, and are membrane permeable, allowing intracellular delivery. Compounds of Formula I may include one or more additional bioactive moieties.

As discussed in more detail below, the novel synthetic method disclosed herein is improved over the previously available methods in that it is simpler and provides better yields than those previously available.

DETAILED DESCRIPTION

Definitions

The following definitions apply to the terms as they are used throughout the specification, unless otherwise indicated.

The terms "alkyl" or "alk," as used herein alone or as part of another group, denote optionally substituted, straight and branched chain saturated hydrocarbon groups, preferably having 1 to 12 carbons in the normal chain, most preferably lower alkyl groups. Exemplary unsubstituted groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl and the like. Exemplary substituents include one or more of the following groups: halo, alkoxy, arylalkyloxy (e.g., benzyloxy), alkylthio, alkenyl, alkynyl, aryl, cycloalkyl, cycloalkenyl, hydroxy, carboxyl (—COOH), amino, alkylamino, dialkylamino, formyl, alkylcarbonyloxy, alkylcarbonyl, heterocyclo, aryloxy or thiol (—SH). Preferred alkyl groups are unsubstituted alkyl, haloalkyl, arylalkyl, aminoalkyl, alkylaminoalkyl, dialkylaminoalkyl, alkyloxyalkyl, aryloxyalkyl, hydroxyalkyl and alkoxyalkyl groups.

The terms "lower alk" or "lower alkyl," as used herein, denote such optionally substituted groups as described above for alkyl having 1 to 4 carbon atoms in the normal chain.

The terms "alkoxy" or "alkylthio" denote an alkyl group as described above bonded through an oxygen linkage (—O—) or a sulfur linkage (—S—), respectively. The term "alkylcarbonyl," as used herein, denotes an alkyl group bonded through a carbonyl group. The term "alkylcarbonyloxy," as used herein, denotes an alkyl group bonded through a carbonyl group which is, in turn, bonded through an oxygen linkage.

The term "alkenyl," as used herein alone or as part of another group, denotes optionally substituted, straight and branched chain hydrocarbon groups containing at least one carbon to carbon double bond in the chain, and preferably having 2 to 10 carbons in the normal chain. Exemplary unsubstituted such groups include ethenyl, propenyl, butenyl, pentenyl, hexenyl, heptenyl, octenyl, nonenyl, decenyl, and the like. Exemplary substituents include one or more alkyl groups as described above, and/or one or more groups described above as alkyl substituents.

The term "alkynyl," as used herein alone or as part of another group, denotes optionally substituted, straight and branched chain hydrocarbon groups containing at least one carbon to carbon triple bond in the chain, and preferably having 2 to 10 carbons in the normal chain. Exemplary unsubstituted such groups include ethynyl, propynyl, butynyl, pentynyl, hexynyl, heptynyl, octynyl, nonynyl, decynyl, and the like. Exemplary substituents include one or more alkyl groups as described above, and/or one or more groups described above as alkyl substituents.

The term "cycloalkyl," as used herein alone or as part of another group, denotes optionally substituted, saturated cyclic hydrocarbon ring systems, preferably containing 1 to 3 rings and 3 to 7 carbons per ring. Exemplary unsubstituted such groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, and/or one or more groups described above as alkyl substituents.

The abbreviation "DEAD" refers to diethylazodicarboxylate.

The term "cycloalkenyl," as used herein alone or as part of another group, denotes such optionally substituted groups as described above for cycloalkyl, further containing at least one carbon to carbon double bond forming a partially unsaturated ring. Exemplary substituents include one or more alkyl groups as described above, and/or one or more groups described above as alkyl substituents.

The terms "ar" or "aryl," as used herein alon& or as part of another group, denote optionally substituted, homocyclic aromatic groups, preferably containing 1 or 2 rings and 6 to 12 ring carbons. Exemplary unsubstituted such groups include phenyl, biphenyl, and naphthyl. Exemplary substituents include one or more, preferably three or fewer, nitro groups, alkyl groups as described above and/or groups described above as alkyl substituents. Preferred aryl groups are unsubstituted aryl and hydroxyaryl.

The term "carbocyclic," as used herein alone or as part of another group, denotes optionally substituted saturated, partially unsaturated or aromatic homocyclic hydrocarbon ring systems such as the cycloalkyl, cycloalkenyl or aryl groups described above.

The terms "heterocyclo" or "heterocyclic," as used herein alone or as part of another group, denote optionally substituted fully saturated or unsaturated, aromatic or non-aromatic cyclic groups having at least one heteroatom in at least one ring, preferably monocyclic or bicyclic groups having 5 or 6 atoms in each ring. The heterocyclo group may, for example, have 1 or 2 oxygen atoms, 1 or 2 sulfur atoms, and/or 1 to 4 nitrogen atoms in the ring. Each heterocyclo group may be bonded through any carbon or heteroatom of the ring system. Preferred groups include those of the following formula, which may be bonded through any atom of the ring system:

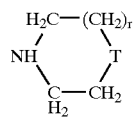

where r is 0 or 1 and T is —O—, —S—, —N—$R^8$ or —CH—$R^8$ where $R^8$ is hydrogen, alkyl, aryl or arylalkyl. Exemplary heterocyclo groups include the following: thienyl, furyl, pyrrolyl, pyridyl, imidazolyl, pyrrolidinyl, piperidinyl, azepinyl, indolyl, isoindolyl, quinolinyl, isoquinolinyl, benzothiazolyl, benzoxazolyl, benzimidazolyl, morpholinyl, piperazinyl, 4-alkylpiperazinyl, 4-alkylpiperidinyl, 3-alkylpyrrolidinyl, oxazolyl, pyrazolyl, thiophenyl, pyridazinyl, thiazolyl, triazolyl, pyrimidinyl, 1,4-dioxanyl, benzoxadiazolyl, and benzofuranyl. Exemplary substituents include one or more alkyl groups as described above and/or one or more groups described above as alkyl substituents.

The terms "halogen," "halo," or "hal," as used herein alone or as part of another group, denote chlorine, bromine, fluorine, and iodine.

The term "acyl," as used herein alone or as part of another group, denotes the moiety formed by removal of the hydroxyl group from the group —COOH of an organic carboxylic acid. Exemplary such groups include alkylcarbonyl, arylcarbonyl, or carbocyclo- or heterocyclo-carbonyl. The term "acyloxy," as used herein alone or as part of another group, denotes an acyl group as described above bonded through an oxygen linkage (—O—).

For the above optionally substituted groups, reference to a specific substituent may be made without excluding the presence of other substituents. Thus, for example, "hydroxyalkyl" is a straight or branched chain saturated hydrocarbon group bearing at least one hydroxy substituent and no other or, optionally, one or more additional, substituents.

The terms "bioactive group" or "bioactive moiety," as used herein, denote a group which is capable of functioning as a metabolic substrate, catalyst, or inhibitor, or is capable of being preferentially taken up at a selected site of a subject, such as by possessing an affinity for a cellular recognition site. Compounds produced by the method disclosed herein contain at least one bioactive group, a hypoxia localizing moiety.

The terms "hypoxia localizing group" or "hypoxia localizing moiety", as used herein denote a specific bioactive group or moiety which is capable of specifically localizing in hypoxic tissue (e.g. tissue which is deficient in oxygen, but still viable). Suitable hypoxia localizing moieties are those which are preferentially retained in regions of a subject which are hypoxic relative to the degree of retention in tissues which are normoxic. Compounds produced by the method disclosed herein contain at least one hypoxia localizing moiety.

The term "linking group," as used herein, denotes a group which, alone or together with one or more other groups, may be used to covalently bond a bioactive group to the remainder of a compound of Formula I.

The various substituents of the ligands of the present invention may be chosen to form stable compounds.

Synthesis of Compounds of Formula I

The synthetic method of the invention is illustrated in the following General Reaction Scheme and in the Example herein.

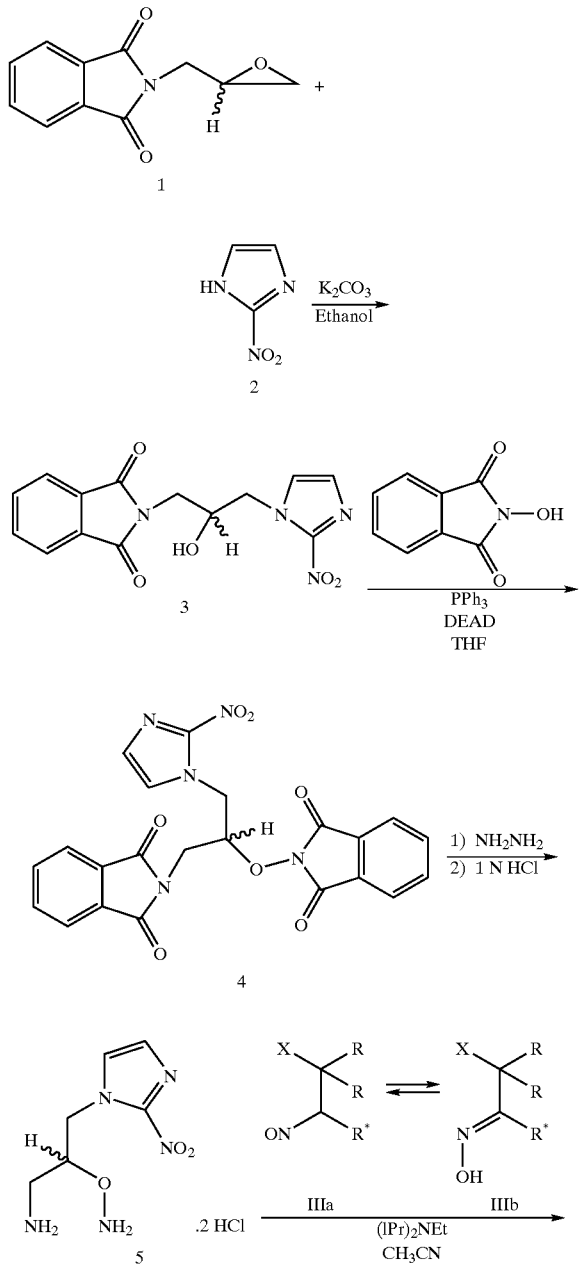

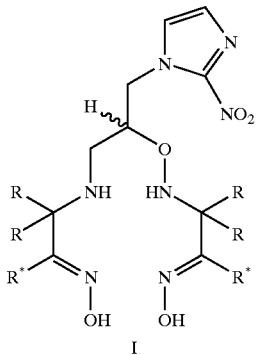

According to the General Reaction Scheme, N-(2,3-epoxypropyl)phthalimide (1) is reacted with 2-nitroimidazole (2) to obtain 2-[2-Hydroxy-2-(2-nitro-1H-imidazol-1-yl)ethyl]-1H-isoindole-1,3(2H)-dione (3). This product is then reacted with N-hydroxyphthalimide, preferably in the presence of a tertiary amine such as triphenylphosphine, to obtain the intermediate of Formula II, 2-{2-(1,3-dioxoisoindolin -2-yl)-1-[(2-nitroimidazolyl)methyl]ethoxy}isoindoline-1,3-dione (4). This intermediate is then reacted with hydrazine to obtain 1-[3-amino-2-(aminooxy)propyl]-2-nitro-1H -imidazole dihydrochloride (5), which is then reacted with the compound of Formula III to yield the compound of Formula I. A preferred compound of Formula III is 3-chloro-3-methyl-2-nitrosobutane, which, when used contacted with 1-[3-amino-2-(aminooxy) propyl]-2-nitro -1H-imidazole dihydrochloride (5), yields 3,3,9,9-tetramethyl-6-[(2-nitro-1H-imidazol-1-yl)methyl]-5-oxa-4,8-diazaundecane-2,10-dione dioxime (7).

Compounds of the Formula III may be prepared by methods such as those described in Vassian, Inorg. Chem., 6, 2043–2046 (1967), Pfleiderer et al., Liebigs Ann. Chem., 99, 3008 (1966), or, especially where R or R* is $CH_3$—, by the method of Nowotnik et al., European Pat. No. 0179608 A2 (1986).

This novel synthetic method provides distinct advantages over previously available methods. For instance, the method simplifies the synthesis with a concomitant reduction in the number of steps necessary to produce the compounds of Formula I. Specifically, the two secondary amines of the novel intermediate of Formula II are both protected as phthalimides, which leads to fewer synthetic steps and higher yield. Unexpectedly, the intermediate of Formula II provides a solubility profile that allows simple extraction to remove impurities, which is experimentally easier than the recrystallization or column chromatography required by previously available methods. Thus, unlike methods that require column chromatography, the synthetic method disclosed herein facilitates large scale synthesis. Additionally, the last step of the synthesis provides a crystalline product and the new experimental features HPLC monitoring of reagents for better control of reaction. In short, the synthetic method disclosed herein is simpler and more efficient than those previously available.

Metal Complexes

The compounds of Formula I may be employed as ligands for the formation of metal complexes. Metal complexes may be formed by complexing a ligand made using the synthetic method of the invention with a radioactive or non-radioactive metal, including metals having an atomic number 22–31, 39–49 or 73–82, especially a radioactive metal, preferably under basic conditions.

Preferred metal complexes are those in which a compound of Formula I is complexed with a radioactive metal, such as technetium or rhenium, most preferably with technetium. Ligands which form single, neutral complexes are preferred. Exemplary complexes include those having the following structure:

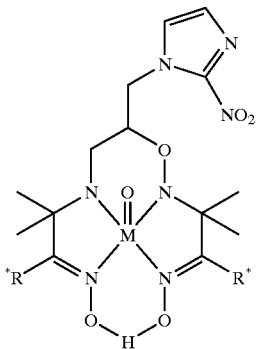

where M is technetium and R and R* are methyl. These metal complexes find utility as diagnostic and/or therapeutic agents. The metal complexes of the present invention may be administered by any appropriate route such as orally, parenterally (for example, intravenously, intraperitoneally, intramuscularly, or subcutaneously), or by any other suitable method. For example, the complexes of this invention may be administered to a subject by bolus or slow infusion intravenous injection.

The amount administered may be selected based on the desired use, such as to produce a diagnostic image of an organ or other site of a subject or a desired radiotherapeutic effect, by methods known in the art. Exemplary dosages are those employing about 30–200 mCi rhenium (for radiotherapy) or about 10–60 mCi technetium (for imaging). The "subject" of the methods of the present invention is preferably a mammal such as a domestic mammal, for example, a dog, cat, horse or the like, or most preferably, a human. Depending upon the metal and ligand used, the complexes of the present invention may be employed as, for example, imaging agents useful for imaging organs such as the heart, brain (where the complex may cross the blood-brain barrier), or the hepatobiliary system. They are especially useful for the imaging of hypoxic tissue, and as therapeutic agents, especially as hypoxic tissue cytotoxins, or radiosensitizers.

An exemplary method for the formation of a metal complex with ligands made from the synthetic method of the present invention is that where a complex or salt of the desired metal in the desired oxidation state and containing one or more easily displaceable (i.e. labile) ligands (for example, $H_2O$, halogen (e.g. Cl), $NO_3^-$, or sugars) is mixed with ligand(s) at a pH value suitable for forming the desired complex. The labile ligand is displaced from the metal by the ligand(s) of the present invention to form a metal complex. Illustrative such methods are shown as follows:

$$(Met)(Lig_{lab})4 + (Lig_{inv}) \rightarrow (Met)(Lig_{inv}) + 4(Lig_{lab}) \quad (1)$$

where

Met is a metal in a desired oxidation state;

$Lig_{lab}$ is a labile ligand such as $H_2O$, $Cl^-$, $Br^-$, $F^-$ or $NO_3^-$; and $Lig_{inv}$ is a ligand made from the synthetic method of the invention.

$$(Met)OCl_4^- + (Lig_{inv}) \rightarrow (Met)O(Lig_{inv}) + 4Cl^- \quad (2)$$

$$(Met)O_2(Lig_{mono})_4 + (Lig_{inv}) \rightarrow (Met)O_2(Lig_{inv}) + 4(Lig_{mono}) \quad (3)$$

where $Lig_{mono}$ is a monodentate ligand such as pyridine, halide, phosphine or amine.

$$(Met)(Lig_{bi})_2 + (Lig_{inv}) \rightarrow (Met)(Lig_{inv}) + 2(Lig_{bi}) \quad (4)$$

or $$(Met)O(Lig_{bi})_2 + (Lig_{inv}) \rightarrow (Met)O(Lig_{inv}) + 2(Lig_{bi}) \quad (5)$$

where $Lig_{bi}$ is a bidentate ligand such as a sugar, a diol, a bisamine, bipyridine or phosphine, and where, for each equation (1) to (5) above, the appropriate charge balance is employed.

Alternatively, metal complexes may be prepared from a metal in an oxidation state different from that of the desired complex. An exemplary such method is that where either a reducing agent or an oxidizing agent (depending on the oxidation state of the metal used, and the oxidation state of the desired final product) is added to the reaction mixture containing metal to bring the metal to the desired oxidation state. The oxidant or reductant may be used to form an intermediate complex in the desired oxidation state but with labile ligands which are then displaced by a desired chelating ligand of the present invention; or the oxidant or reductant may be added to the reaction mixture containing metal along with the desired ligand to achieve the change to the desired oxidation state and chelation to the desired metal in a single step.

Rhenium complexes are particularly useful in radiotherapy agents. The rhenium employed is preferably one of the radionuclides Re-186 or Re-188, or a mixture thereof, which mixture may also include Re-185 and/or Re-187. Preparation of the complexes of the present invention where the metal is rhenium may be accomplished using rhenium in the +5 or +7 oxidation state. Examples of compounds in which rhenium is in the Re(VII) state are $NH_4ReO_4$ or $KReO_4$. Re(V) is available as, for example, $[ReOCl_4]$ $(NBu_4)$, $[ReOCl_4](AsPh4)$, $ReOCl_3(PPh_3)_2$ and as $ReO_2$ $(pyridine)_4^+$. (Ph is phenyl; Bu is n-butyl). Other rhenium reagents capable of forming a rhenium complex may also be used. The use of "carrier rhenium" is preferred. The phrase "carrier rhenium" means that the rhenium compounds used contain non-radioactive rhenium at concentrations $>10^{-7}$ M.

Technetium complexes are particularly useful in radiodiagnostic imaging agents. The technetium employed is preferably one or more of the radionuclides $^{99m}Tc$, $^{94m}Tc$ or $^{96}Tc$-. The preferred radioisotope for medical imaging is $^{99m}Tc$. Its 140 keV γ-photon is ideal for use with widely available gamma cameras. It has a short (6 hour) half-life, which is desirable when considering patient dosimetry. $^{99m}Tc$ is readily available at relatively low cost through commercially produced $^{99}Mo/^{99m}Tc$ generator systems. Preparation of the complexes of this invention where the metal is technetium may be accomplished using technetium in the form of the pertechnetate ion. For $^{99m}Tc$, the pertechnetate ion is preferably obtained from commercially available technetium-99m parent-daughter generators; such technetium is in the +7 oxidation state. The generation of the pertechnetate ion using this type of generator is well known in the art, and is described in more detail in U.S. Pat. Nos. 3,369,121 and 3,920,995. These generators may generally be eluted with saline solution, and the pertechnetate ion obtained as the sodium salt. Pertechnetate may also be prepared from cyclotron-produced radioactive technetium using procedures well known in the art.

The formation of a technetium complex is preferably achieved by mixing pertechnetate ion in normal saline with the appropriate ligand, preferably a ligand of Formula I. An appropriate buffer or physiologically acceptable acid or base may be used to adjust the pH to a value suitable for labeling the ligand. This appropriate value of pH will vary depending upon the nature of the ligand; for example, for ligands of Formula I, a pH in the range between approximately equal to 5.5 to approximately equal to 9.5 is suitable, preferably a pH value in the range of 7.0 to 8.5. A source of reducing agent may then be added to bring the pertechnetate down to the oxidation state of Tc(V) for chelation with the ligand. Stannous ion is the preferred reducing agent, and may be introduced in the form of a stannous salt such as stannous chloride, stannous fluoride, stannous tartrate, stannous diethylenetriamine pentaacetic acid (stannous DTPA), or stannous citrate, or the like. The reaction is preferably run in an aqueous or aqueous/alcohol mixture, at or about room temperature, using a reaction time of about 1 minute to about 1 hour. The reducing agent is preferably present at a concentration of 5 to 50 $\mu$g/mL. The ligand is preferably present in a concentration of 0.5 to 2 mg/mL. Optionally, co-ligands may be added.

Alternatively, the technetium complexes produced from ligands made by the synthetic method of the invention may be prepared by ligand exchange. A labile Tc(V) complex may be prepared by the reduction of $TcO_4^-$ in the presence of a ligand which forms a labile technetium complex, such as ethylene glycol, mannitol, or the hydroxycarboxylate ligands glucoheptonate, gluconate, citrate, malate or tartrate, at a pH value which is appropriate for the exchange ligand employed (usually 5 to 8). A reducing agent, such as the stannous salts described above, may be added, causing the formation of a labile reduced complex of Tc with the exchange ligand. This reduced Tc complex is then mixed with the ligand of Formula I at an appropriate pH value (as described above). The labile exchange ligand is displaced from the metal by the desired ligand, thus forming the technetium complexes of this invention.

Bioactive Moieties

A bioactive group as used herein is capable of functioning as a metabolic substrate, catalyst or inhibitor, for example, to aid in clearance of the complex from non-target tissue; or is capable of being preferentially taken up at a selected site of a subject, such as by possessing an affinity for a cellular recognition site such as a receptor, enzyme, or transport mechanism, or by containing reactive groups for coupling to proteins, or tissue localization by another biochemical process. Thus, complexes of the present invention are contemplated where one or more bioactive groups are bound to the remainder of the complex, such that the one or more bioactive groups retain their desired bioactivity when so bound.

Exemplary bioactive groups include amphetamines, barbiturates, sulfonamides, monoamine oxidase substrates and inhibitors, hormones, enzymes, lipids, ligands for cell membrane receptors, antihypertensives, neurotransmitters, amino acids and oligopeptides, radiosensitizers, steroids (such as estrogen or estradiol), interchelators, monoclonal or polyclonal antibodies or fragments thereof, sugars (such as glucose derivatives), fatty acids, substrates for muscarinic receptors (such as 3-quinuclidinyl benzilate), substrates for dopamine receptors (such as spiperone), biotin, chemotactic peptides, substrates for benzodiazepine receptors and, especially, hypoxia-localizing moieties described further below.

Examples of diagnostic uses for the complexes prepared by the synthetic method of the invention include, but are not limited to, imaging of hypoxic tissue, e.g., in the heart, brain, lungs or in tumors, preferably where the complexes contain a nitro-heterocyclic group trapped by hypoxia-mediated reduction of the nitro moiety (referred to herein as a "hypoxia-mediated nitro-heterocyclic group"), discussed further below; imaging of the brain and lungs when the bioactive group is a lipophilic amine-containing compound, e.g. an amphetamine; imaging of the brain, heart or tumors when the bioactive group is a sugar (e.g., a glucose derivative); imaging of the heart when the bioactive group is a fatty acid; imaging of steroid receptor sites when the bioactive group is a steroid (e.g., an estrogen for imaging breast carcinoma); and imaging of sites of infection when the bioactive group is a chemotactic peptide with affinity for blood cell types which localize at the site of infection.

In addition to diagnostic agents, the synthetic method of the invention also provides stably bound complexes for radiotherapeutic indications, especially where the metal is Re, such as those indications described in U.S. Pat. No. 4,871,836. For example, Re complexes which include estradiols can be used in the treatment of breast carcinoma. Also, to the extent that hypoxic tissue is known to be present in tumors, Re complexes of the present invention where the bioactive group is a hypoxia-localizing moiety are suitable for radiotherapy.

Hypoxia-Localizing Moieties

Compounds prepared by the synthetic method of the invention will include at least one hypoxia-localizing moiety, which specifically localizes in hypoxic tissue, e.g. tissue which is deficient in oxygen but still viable. These compounds may thus be used in diagnostic methods to obtain information about the state of such tissue.

Suitable hypoxia-localizing moieties are those which are preferentially retained in regions of a subject which are hypoxic relative to the degree of retention in regions which are normoxic. The greater the selective localization in hypoxic versus normoxic tissue, the more accurate the information provided. Compounds prepared by the method of the invention are derivatized with a 2-nitro-imidazole hypoxia-localizing moiety. However, other useful hypoxia localizing moieties include 4- and 5-nitro-imidazoles, as well as nitrofuran, nitrothiazole and nitrotriazole derivatives. Exemplary groups are described in U.S. Pat. No. 5,608,110.

Radiopharmaceuticals containing such hypoxia localizing moieties will display relatively high concentrations in such hypoxic regions, with low concentrations in normoxic and infarcted regions. Complexes which concentrate rapidly in hypoxic tissue and which remain stably bound in such tissue over time, while exhibiting a lack of binding and rapid washout from normoxic tissue, are preferred.

Exemplary diagnostic uses for such complexes, especially where the metal complexed is technetium, include imaging of hypoxic tissue present under pathological conditions in areas such as the heart, brain, lungs, liver, kidneys or in tumors, or in peripheral vascular diseases such as diabetes. In the brain or heart, hypoxia typically follows ischemic episodes produced by, for example, arterial occlusions or by a combination of increased demand and insufficient flow. Diagnostic imaging with radiopharmaceuticals of the present invention possessing hypoxia-localizing moieties allows the identification of tissue which is at risk of progressing to infarction, but still salvagable in such areas.

Additionally, tumors often have regions within their mass which are hypoxic. These result when the rapid growth of the tumor is not matched by the extension of tumor vasculature. Radiopharmaceuticals that localize preferentially within regions of hypoxia may also therefore be used to provide images which are useful in the diagnosis and management of therapy of tumors. Further, a compound which localizes within the hypoxic region of tumors, and which is labeled with a radionuclide with suitable α- or β-emissions, may be used for the internal radiotherapy of tumors. Stably bound complexes where Re is the radiometal complexed are particularly useful for radiotherapeutic indications where hypoxic tissue is known to be present in tumors.

In addition to being useful in imaging hypoxic tissue, the present complexes may also be used as blood flow markers, that is, for perfusion imaging. The initial distribution of the novel complexes may be proportional to blood flow and therefore imaging carried out soon after administration may be used as an indicator of perfusion. A short time later, as the complexes wash out of the normoxic tissue but are retained in the hypoxic tissue, imaging of the hypoxic tissue is realized.

Linking Groups

The linking group(s) $(A)_p$ of the compounds made using the synthetic method of the invention, when present (that is, when p is greater than zero), may be any one or more moieties which can serve to physically distance, or otherwise isolate, a bioactive group from the remainder of the compound of Formula I or complex thereof. The presence of such linking group(s) may be desirable, for example, where a bioactive group may be inhibited in its action by the remainder of the complex. In considering the various linking groups that may be employed, it is understood that p may be any convenient value depending upon the design choice for the desired complex. Preferably, p is ≦20 and is most preferably ≦10.

Preferred linking groups which may be employed alone (where p is one), or together to form a straight or branched chain (where p is greater than one) and which may be bonded to the remainder of the ligand from either end are: —CH$_2$—, —CHR$^5$—, —CR$^5$R$^6$—, —CH=CH—, —CH=CR$^5$—, —CR$^5$=CR$^6$—, —C≡C—, cycloalkyl, cycloalkenyl, aryl (e.g., p-phenylene or hydroxy substituted p-phenylene), heterocyclo, oxygen, sulfur, —C(O)—, —NH—, —HC=N—, —CR$^5$=N—, —NR$^5$—, or —CS—; wherein R$^5$ and R$^6$ are independently selected from alkyl, alkenyl, alkoxy, aryl, 5- or 6-membered nitrogen- or oxygen-containing heterocycles, halogen, hydroxy or hydroxyalkyl.

In the complexes of the present invention, the preferred values for $(A)_p$ (bonded to the remainder of the ligand from either end) are alkyl, oxa-alkyl, hydroxyalkyl, hydroxyalkoxy, alkenyl, arylalkyl, arylalkylamide, alkylamide, alkylamine and (alkylamine)alkyl.

The most preferred values for $(A)_p$ are selected from the following (bonded to the remainder of the ligand from either end): —(CH$_2$)$_{1-5}$—, (especially methyl or ethyl, particularly when bonded to a hypoxia-localizing moiety), —CH$_2$—CH=CH—CH$_2$—, —(CH$_2$)$_{1-2}$—C(O)—NH—(CH$_2$)$_{1-3}$—, —C$_6$H$_5$—(CH$_2$)$_{1-2}$—, —(CH$_2$)$_{1-2}$—CH(OH)—CH$_2$—, —(CH$_2$)$_2$—O—, —CH$_2$CH(OH)CH$_2$OCH$_2$—, —CH$_2$—C(O)—NH—CH—C$_6$H$_5$—, —(A'—O—A")$_{1-3}$, and —(A'—NH—A")$_{1-3}$; where A' and A" are the same or different alkyl or aryl groups and C$_6$H$_5$ is p-phenylene.

Stereoisomers

All stereoisomers of the compounds and complexes of the present invention are contemplated herein, whether alone (that is, substantially free of other isomers), in a mixture of certain stereoisomers (for example, as a racemate) or in any other mixture thereof. Stereoisomeric mixtures may be separated, for example, by use of a suitable chiral column. The R and S isomers of the compounds of Formula I may also be prepared employing chiral starting materials or intermediates as shown below.

Synthetic Scheme for the preparation of S isomers of compounds of Formula I:

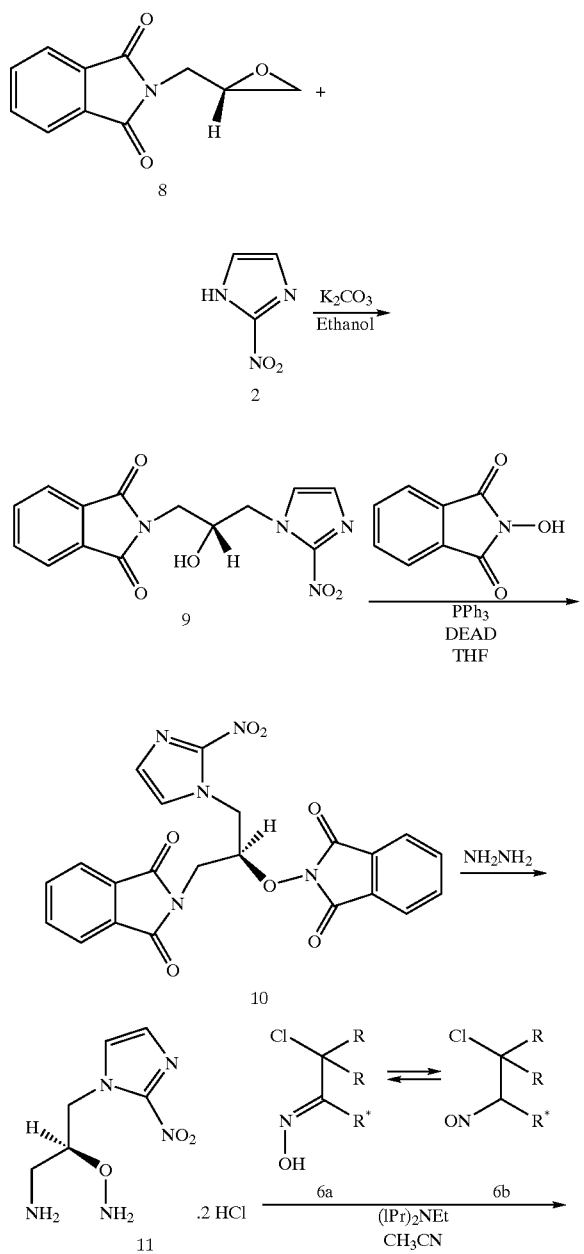

15

-continued

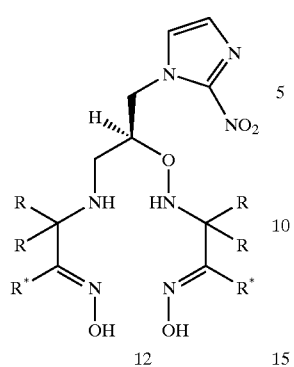

12

This method may be used to produce the S isomer of Compound Ia, [(S)-(−)-3,3,9,9-Tetramethyl-6-[(2-nitro-1H-imidazol-1-yl)methyl]-5-oxa-4,8-diazaundecane-2,10-dione dioxime], starting from (R)-2-Oxyranylmethyl__1-H__isoindole-1,3-(2H)-dione (8) where R and R* in Compound 6a/6b are methyl. This method may also be used to isolate and/or purify the intermediate compound 2-{(1R)-2-(1,3-dioxoisoindolin-2-yl)-1-[(2-nitroimidazolyl)methyl]ethoxy}isoindoline-1,3-dione (10).

Synthetic Scheme for the preparation of R isomers of compounds of Formula I:

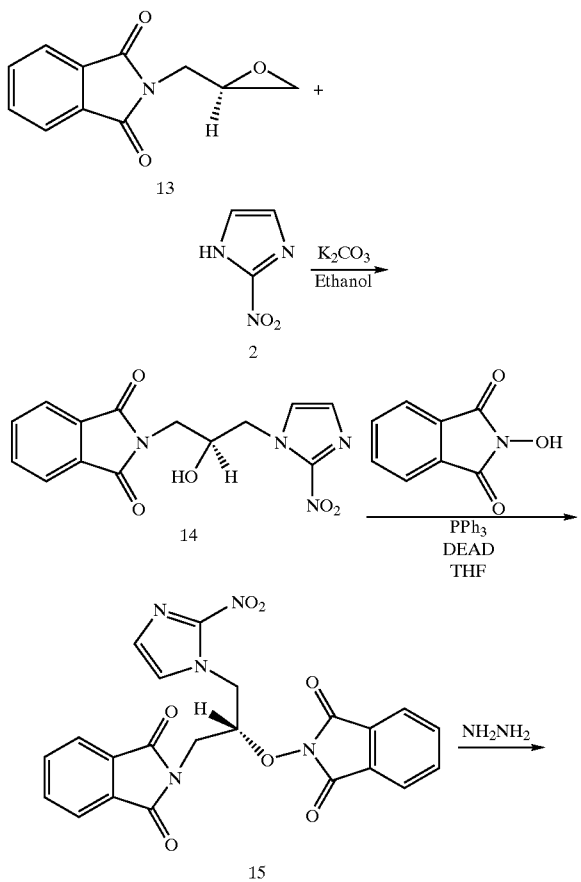

16

-continued

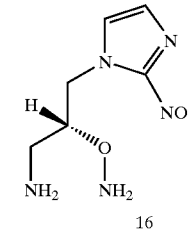

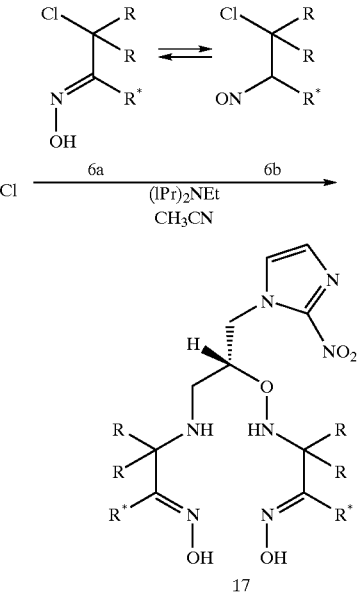

17

This method may be used to produce the R isomer of Compound Ia, [(R)-(−)-3,3,9,9-Tetramethyl-6-[(2-nitro-1H-imidazol-1-yl)methyl]-5-oxa-4,8-diazaundecane-2,10-dione dioxime], starting from (S)-2-Oxyranylmethyl__1-H__isoindole-1,3-(2H)-dione (13) where R and R* in Compound 6a/6b are methyl. This method may also be used to isolate and/or purify the intermediate compound 2-{(1S)-2-(1,3-dioxoisoindolin-2-yl)-1-[(2-nitroimidazolyl)methyl]ethoxy}isoindoline-1,3-dione (15).

EXAMPLE

The following reaction scheme was followed to prepare 3,3,9,9-Tetramethyl-6-[(2-nitro-1H-imidazol-1-yl)methyl]-5-oxa-4,8-diazaundecane-2,10-dione dioxime:

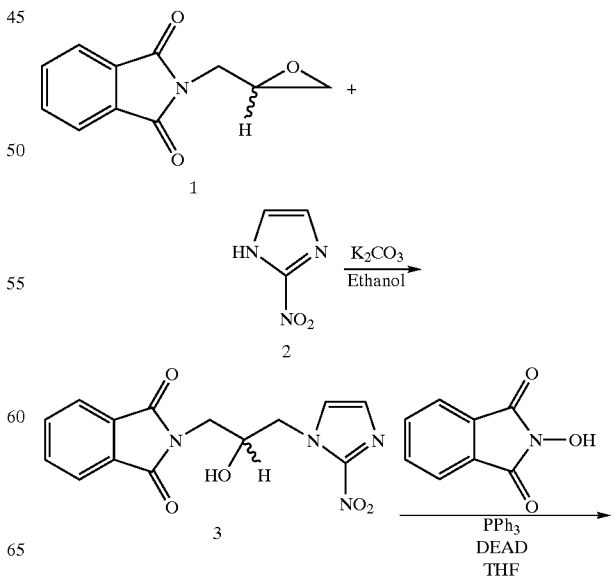

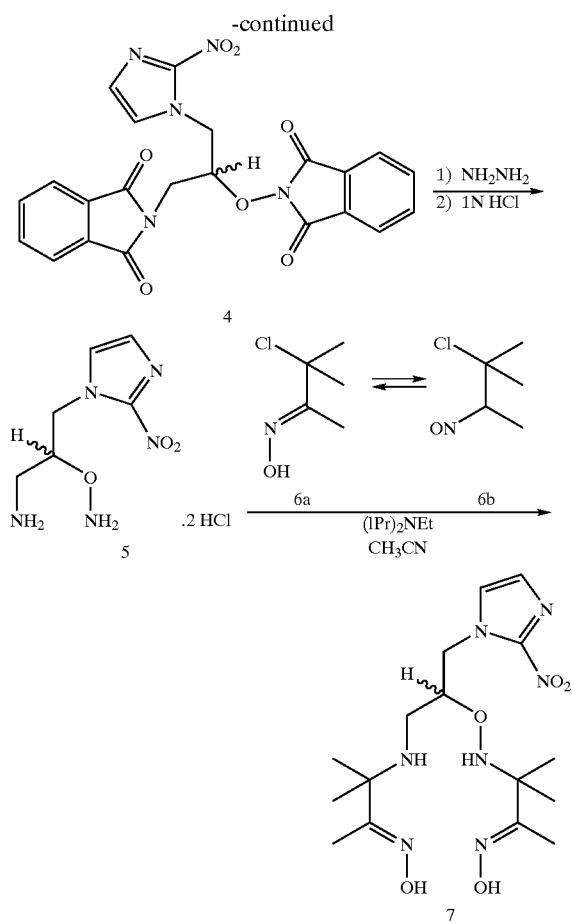

Synthesis of 3,3,9,9-Tetramethyl-6-[(2-nitro-1H-imidazol-1-yl)methyl]-5-oxa-4,8-diazaundecane-2,10-dione dioxime

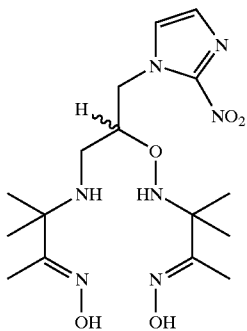

A. Preparation of 2-[2-hydroxy-2-(2-nitro-1H-imidazol-1-yl)ethyl]-1H-isoindole-1,3(2H)-dione To a solution of N-(2,3-epoxypropyl)phthalimide (1) (Fluka, 25.0 g, 0.123 mol) in ethanol (200 mL), 2-nitroimidazole (2) (Nippon Ghosei, 14.5 g, 0.128 mol) and potassium carbonate (1.5 g) were added, and the reaction mixture was heated under reflux for 8 hrs. The reaction mixture was cooled and the yellow solid obtained was filtered and washed with ethanol (2×75 mL). The precipitate was transferred to a one liter beaker and water was added (500 mL). The mixture was stirred for 15 min. The yellow precipitate was filtered and the solid was washed with water (3×250 mL). 2-[2-hydroxy-2-(2-nitro-1H-imidazol-1-yl) ethyl]-1H-isoindole-1,3(2H)-dione (3) was obtained and dried under vacuum. Yield 32.8 g (85%). The product was pure by proton NMR and HPLC, and was used in the next step without further purification. A portion (~2 g) of the solid was recrystallized from methanol. The melting point was 213–214° C.

$^1$H NMR (DMSO): δ3.62 (m, 2H, PhthNCH$_2$CHOH), 4.08 (m, 1H, CHOH), 4.32 and 4.63 (m, 2H, CHOHCH$_2$N<), 5.54 (d, 1H, CHOH), 7.15 and 7.68 (s, 2H, imiH), 7.8 (m, 4H, ArH).

MS: (M+H)$^+$=317$^+$ (M+Na)$^+$=339$^+$

B. Preparation of 2-{2-(1,3-dioxoisoindolin-2-yl)-1-[(2-nitroimidazolyl)methyl]ethoxy}isoindoline-1,3-dione To a slurry of 2-[2-hydroxy-2-(2-nitro-1H-imidazol-1-yl) ethyl]-1H-isoindole-1,3(2H)-dione (3) (6.3 g, 0.02 mol) and N-hydroxyphthalimide (4.0 g, 0.0245 mol) in THF (100 mL), triphenylphosphine (7.5 g, 0.028 mol) was added and the mixture was stirred at room temperature for 15 min. The mixture was then cooled to −5° C. and diethylazodicarboxylate (4.95 g, 4.5 mL, 0.028 mol) was added slowly via syringe. The temperature of the reaction mixture rose to 0° C. and the mixture was then stirred at 0° C. for 12 h. The solid formed was then filtered, washed with cold THF (−20° C., 100 mL), and dried to obtain 6.0 g (65%) of the crude product.

HPLC analysis of the crude product obtained indicated the presence of unreacted N-hydroxyphthalimide as an impurity. The crude product was dissolved in methylene chloride (200 mL) and washed with a 10% solution of sodium carbonate (3×75 mL), washed with water and dried (Na$_2$SO$_4$). Evaporation of methylene chloride gave 5.4 g (58.7%) of pure 2-{2-(1,3-dioxoisoindolin-2-yl)-1-[(2-nitroimidazolyl)-methyl]-ethoxy}isoindoline-1,3-dione (4) which was used in the next step without further purification. A portion of the 2-{2-(1,3-dioxoisoindolin-2-yl)-1-[(2-nitroimidazolyl)methyl]ethoxy}isoindoline-1,3-dione (4) was recrystallized from ethyl acetate. The melting point was 119–121° C.

$^1$HNMR (CDCl$_3$): δ4.1 (m, 2H, NCH$_2$CHO), 4.7 (1H, NCH$_2$CHO), 4.88 (m, 2H, CH$_2$Nphth), 7.25 and 7.27, (2s, 2H, imiH), 7.7–7.8 (m, 8H, ArH).

MS: (M+H)$^+$=462.1

Anal. Calcd. for C$_{22}$H$_{15}$N$_5$O$_7$: C, 57.27;H, 3.28; N, 15.18; O, 24.27% Found: C, 56.81, H, 3.17; N, 15.02%

C. Preparation of 1-[3-amino-2-(aminooxy)propyl]-2-nitro-1H-imidazole

To a slurry of 2-{2-(1,3-dioxoisoindolin-2-yl)-1-[(2-nitroimidazolyl)methyl]ethoxy}isoindoline-1,3-dione (4) (2.3 g, 0.005 mol) in methanol (20.0 mL) was added hydrazine monohydrate (0.625 g, 0.0125 mol) and the mixture was heated at 80° C. A clear solution was formed in 10 min. and a yellow solid began to separate (~20 min). The heating was continued for 3 h and the yellow solid formed was filtered, washed with methanol, and dried under vacuum. The yellow solid (later identified as the adduct of phthalylhydrazide and the diamine, mp. 214–216° C.) obtained was suspended in hydrochloric acid (1N, 100 mL) and stirred at room temperature for 15 min. The white precipitate formed was filtered and the filter cake was washed with water (2×10 mL). The filtrate and washings were combined and concentrated under vacuum to give 1-[3-amino-2-(aminooxy)propyl]-2-nitro-1H-imidazole dihydrochloride (5) as a white solid. Absolute ethanol (10 mL) was added to this solid and the ethanol was removed on a rotary evaporator. This process was repeated again and the hydrochloride obtained was dried under vacuum for 24 h. This was used in the next step without further purification. Yield 1.12 g (82%). A portion of the hydrochloride was crystallized from methanol ether. The melting point was 143–44° C. (dec).

$^1$HNMR (DMSO): δ[3.25 m, 2H, (CHOCH$_2$NH$_3^+$)$_2$], 4.9 (m, 3, CHOCH$_2$ imi), 7.15 and 7.72(s, 2H, imiH), 8.5 (bs, 6H, NH$_3^+$).

MS: (M+H)$^+$=202

D. Preparation of 3-chloro-3-methyl-2-nitrosobutane

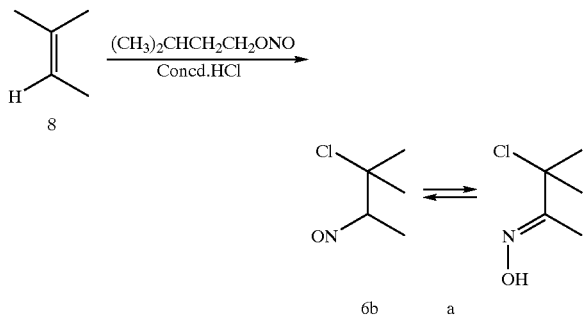

3-chloro-3-methyl-2-nitrosobutane was prepared according to Nowotnik et al., European Pat. No. 0179608 A2 (1986).

A 250 mL 3-necked flask fitted with a mechanical stirrer, a dropping funnel, and a thermometer was charged with 2-methyl-2-butene (8)(27.5 mL, 18.2 g, 0.259 mol) and isoamyl nitrite (32.5 mL, 28.3 g, 0.242 mol). The mixture was then cooled to –15° C. and concentrated HCl (27 mL, 0.329 mol) was added dropwise over a period of 30 min maintaining the temperature at –10° C.–5° C. The light blue slurry was stirred at –10° C.~–5° C. for an additional 30 min. The wet product was dissolved in petroleum ether (bp 30–60° C., 150 mL). The bottom aqueous layer was removed and the organic layer was dried (Na$_2$SO$_4$). The petroleum ether solution was filtered and cooled to –50° C. with occasional stirring, and the white crystalline solid formed was collected by filtration, washed with cold (–50° C.) petroleum ether and dried under vacuum at RT overnight. Yield 18.4 g (56%). mp. 72–73° C., lit. 72.5–74° C.

$^1$HNMR (CDCl$_3$); δ1.50 [d, 3H, CHNOCH$_3$)], 1.65 and 1.69 [2 s, 6H, C(CH$_3$)$_2$], 5.97 (q, 1H, CHNO)

E. Preparation of 3,3,9,9-tetramethyl-6-[(2-nitro-1H-imidazol-1-yl)methyl]-5-oxa-4,8-diazaundecane-2,10-dione dioxime In a nitrogen-flushed, 50-mL, round-bottomed flask equipped with a magnetic stirrer was charged 1-[3-amino-2-(aminooxy)propyl]-2-nitro-1H-imidazole dihydrochloride (5) (1.37 g, 0.005 mol) and acetonitrile (15.0 mL). To the white suspension, diisopropylethylamine (4.29 g, 5.95 mL, 0.033 mol) was added. 3-chloro-3-methyl-2-nitrosobutane (6) (1.5 g, 0.011 mol) was. then added to this mixture and the mixture stirred at room temperature. The progress of the reaction was monitored by HPLC. An aliquot of the reaction mixture was withdrawn after 30 min. HPLC analysis indicated the disappearance of the dihydrochloride and the formation of the mono oxime at $t_R$ 14.47 (80.5%) min, and the product (17%) $t_R$=22.02 min. After 6 hr of the elapsed reaction time the percentage of intermediate mono oxime at $t_R$=14 47 (confirmed by LC mass spec) had changed (45.9%). Using HPLC for monitoring the reaction progress, additional chloro-3-methyl-2-nitrosobutane (0.3 g in 2×0.15 g portions) was added until the reaction was judged complete (disappearance of the mono oxime at $t_R$=14.47 min). Acetonitrile was then removed on a rotary evaporator and the thick oil obtained was basified with saturated potassium carbonate solution (2.5 g, in 25 mL of water). The light green oil obtained was extracted with ethyl acetate and dried (Na$_2$SO$_4$). Ethyl acetate was removed on a rotary evaporator and the oil obtained was dissolved in acetonitrile (5.0 mL) and the acetonitrile was removed by rotary evaporation. This process was repeated again and the viscous oil obtained was dried under vacuum for 24 h to give a foamy solid The foamy solid was dissolved in acetonitrile (7.0 mL) and left at room temperature for 2 h. The dioxime (7) that formed was filtered and recrystallized from acetonitrile. Yield: 1.2 g(60.%). mp. 170–71° C.

$^1$HNMR (DMSO-d$_6$): δ0.96 and 1.11 [s, 12H, C(CH$_3$)$_2$], 1.65 (s, 6H, CH$_3$), 2.30 (m, 2H, HNCH$_2$CHOH), 3.80 (m, 1H, CHO), 4.5 (m, 2H, CHOHCH$_2$N<), 7.15 and 7.59 (s, 2H, imiH) 10.43 (s, 2H, NOH).

MS: (M+H)$^+$=400.2

Anal. Calcd. for C$_{16}$H$_{29}$N$_7$O$_5$: C, 48.11;H, 7.32; N, 24.55; O, 20.03%. Found C, 48.47; H, 7.11; N, 24.59.

Other Embodiments

From the foregoing description, it will be apparent that variations and modifications may be made to the invention described herein to adopt it to various usages and conditions.

INCORPORATION BY REFERENCE

All publications, patents, and patent applications mentioned in this specification are herein incorporated by reference to the same extent as if each independent publication, patent, or patent application was specifically and individually indicated to be incorporated by reference.

What is claimed is:

1. A compound having the structure of Formula II:

II

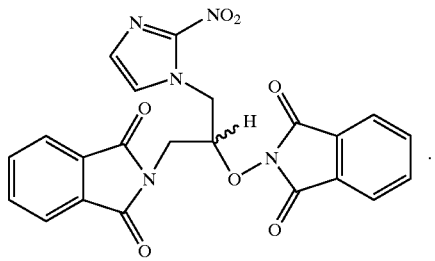

2. The compound of claim 1, having the structure:

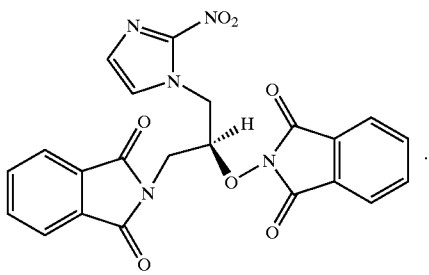

3. The compound of claim 1, having the structure:

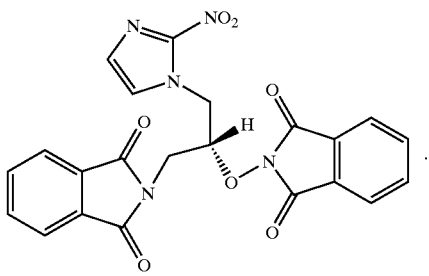

4. A method of synthesizing a compound of claim 1 having the structure Formula II:

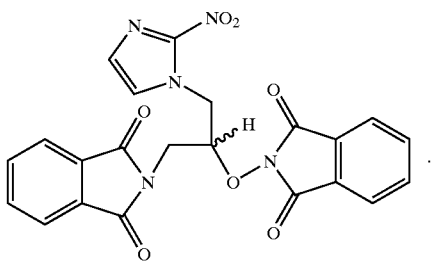

II the method comprising the steps of:
(i) contacting N-(2,3-epoxypropyl)phthalimide with 2-nitroimidazole to obtain 2-[2-hydroxy-2-(2-nitro-1H-imidazol-1-yl)ethyl]-1H-isoindole-1,3(2H)-dione; and
(ii) contacting the product of (i) with N-hydroxyphthalimide to obtain 2-{2-(1,3-dioxoisoindolin-2-yl)-1-[(2-nitroimidazolyl)methyl] ethoxy}isoindoline-1,3-dione.

5. The method of claim 4, wherein the compound has the structure

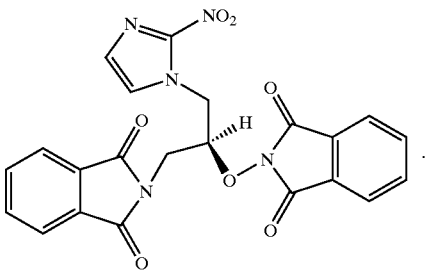

the method comprising the steps of
(i) contacting (R)-2-Oxyranylmethyl_1-H_isoindole-1,3-(2H)-dione with 2-nitroimidazole to obtain 2-[(2S)-2-hydroxy-2-(2-nitro-1H-imidazol-1-yl)ethyl]-1H-isoindole-1,3(2H)-dione; and
(ii) contacting the 2-[(2S)-2-hydroxy-2-(2-nitro-1H-imidazol-1-yl)ethyl]-1H-isoindole-1,3(2H)-dione with N-hydroxyphthalimide to obtain 2-{(1R)-2-(1,3-dioxoisoindolin-2-yl)-1-[(2-nitroimidazolyl)methyl] ethoxy}isoindoline-1,3-dione.

6. The method of claim 4, wherein the compound has the structure

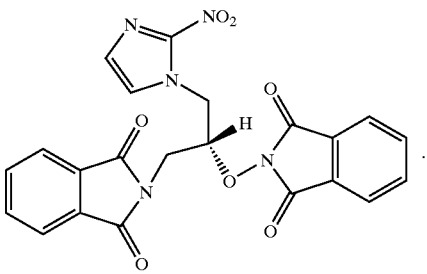

the method comprising the steps of:
(i) (S)-2-Oxyranylmethyl_1-H_isoindole-1,3-(2H)-dione with 2-nitroimidazole to obtain 2-[(2R)-2-hydroxy-2-(2-nitro-1H-imidazol-1-yl)ethyl]-1H-isoindole-1,3(2H)-dione; and
(ii) contacting the 2-[(2R)-2-hydroxy-2-(2-nitro-1H-imidazol-1-yl)ethyl]-1H-isoindole-1,3(2H)-dione with N-hydroxyphthalimide to obtain 2-{(1S)-2-(1,3-dioxoisoindolin-2-yl)-1-[(2-nitroimidazolyl)methyl] ethoxy}isoindoline-1,3-dione.

* * * * *